(12) United States Patent
Bakry

(10) Patent No.: US 10,624,994 B2
(45) Date of Patent: Apr. 21, 2020

(54) BORATE BIOACTIVE GLASS AND METHODS OF USE FOR DENTIN AND ENAMEL RESTORATION

(71) Applicant: King Abdulaziz University, Jeddah (SA)

(72) Inventor: Ahmed Samir Ibrahim Bakry, Jeddah (SA)

(73) Assignee: King Abdulaziz University, Jeddah (SA)

( * ) Notice: Subject to any disclaimer, the term of this patent is extended or adjusted under 35 U.S.C. 154(b) by 181 days.

(21) Appl. No.: 15/690,581

(22) Filed: Aug. 30, 2017

(65) Prior Publication Data

US 2019/0060523 A1    Feb. 28, 2019

(51) Int. Cl.

| | |
|---|---|
| *A61L 27/54* | (2006.01) |
| *A61L 27/10* | (2006.01) |
| *A61L 27/02* | (2006.01) |
| *A61L 27/38* | (2006.01) |
| *A61L 27/12* | (2006.01) |
| *A61C 5/00* | (2017.01) |
| *A61F 2/28* | (2006.01) |
| *A61L 27/24* | (2006.01) |
| *A61L 27/20* | (2006.01) |
| *A61C 8/00* | (2006.01) |
| *A61C 5/20* | (2017.01) |
| *C03C 3/19* | (2006.01) |
| *A61L 27/50* | (2006.01) |
| *C03C 4/00* | (2006.01) |

(52) U.S. Cl.
CPC ............... *A61L 27/54* (2013.01); *A61C 5/00* (2013.01); *A61F 2/28* (2013.01); *A61L 27/025* (2013.01); *A61L 27/10* (2013.01); *A61L 27/12* (2013.01); *A61L 27/20* (2013.01); *A61L 27/24* (2013.01); *A61L 27/3834* (2013.01); *A61L 27/50* (2013.01); *C03C 3/19* (2013.01); *C03C 4/0014* (2013.01); *C03C 4/0021* (2013.01); *A61C 5/20* (2017.02); *A61C 8/0012* (2013.01); *A61F 2002/2835* (2013.01); *A61L 2300/102* (2013.01); *A61L 2300/412* (2013.01); *A61L 2300/606* (2013.01); *A61L 2430/02* (2013.01)

(58) Field of Classification Search
CPC ....... A61L 27/50; A61L 27/10; A61K 6/0276; C03C 3/19; C03C 4/0014; C03C 4/0021
See application file for complete search history.

(56) References Cited

U.S. PATENT DOCUMENTS 5,296,026 A     3/1994     Monroe et al.

FOREIGN PATENT DOCUMENTS

| EP | 2 695 623 A1 | 2/2014 |
| EP | 2 832 342 A2 | 2/2015 |
| WO | 2012/039592 A1 | 3/2012 |
| WO | WO 2014/159240 | * 10/2014 |
| WO | WO 2015/188252 | * 12/2015 |

OTHER PUBLICATIONS

Iulia Mirela Britchi et al., "Factors that Influence the Adherence of Biovitroceramic Coatings on Titanium," Advanced Materials Research, vol. 23, 2007, 2 Pages.

* cited by examiner

*Primary Examiner* — C Melissa Koslow

(74) *Attorney, Agent, or Firm* — Oblon, McClelland, Maier & Neustadt, L.L.P.

(57) ABSTRACT

A borate bioactive glass is described, and may be used in the form of particles in an acidic mixture to form a borate bioactive glass paste. The borate bioactive glass paste may be used for the restoration of dentin and enamel on a tooth surface by the precipitation of calcium phosphate. The borate bioactive glass may also be used as a bone grafting material.

17 Claims, 7 Drawing Sheets

BORATE BIOACTIVE GLASS AND METHODS OF USE FOR DENTIN AND ENAMEL RESTORATION

BACKGROUND OF THE INVENTION

Technical Field

The present invention relates to a borate bioactive glass and method of use in dental restoration and bone grafting.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Treatment of dentin hypersensitivity is one of the major problems faced by dentists worldwide. See Orchardson R, et al., *J Am Dent Assoc.*, 137, 990 (2006)—incorporated herein by reference in its entirety. Moreover, dental caries are one of the most prevalent diseases in the world. See Bakry A S, et al., *J Dent.*, 42, 1458 (2014)—incorporated herein by reference in its entirety. Many agents have been employed for the treatment of both problems; however, more research is needed to explore more options for providing advantageous solutions for these challenges.

Dentin hypersensitivity results from a loss of the overlying enamel coronal tissues by non-cariogenic processes, combined with the subsequent exposure of the underlying dentin tissues to the oral cavity. See Bakry A S, et al., *J Dent Res.*, 90, 246 (2011)—incorporated herein by reference in its entirety. This condition causes exposure of a large number of fluid-filled dentinal tubules to the oral cavity. The hydrodynamic theory of dentin hypersensitivity is the most widely accepted explanation of the condition, and is based on the movement of these fluids. For example, a sudden change in temperature or pH in the oral cavity may result in a rapid movement of these dentinal fluids, and this rapid movement causes the activation of nerve fibers located in close proximity to the odontoblastic cells. These cells are present in the deepest portions of the dentinal tubules, and it is the activation of these nerve fibers that causes the feeling of sharp pain when a patient with dentin hypersensitivity drinks fluids having different temperatures and/or pH. See Brannstrom M, et al., *J Dent Res.*, 47, 679, (1968)—incorporated herein by reference in its entirety.

Based on the current research and clinical observation, the most successful strategy to treat dentin hypersensitivity is to block the orifices of the dentinal tubules exposed to the oral cavity, in order to stop the fluid movement within the dentinal tubules. See Bakry A S, et al., *J Dent Res.*, 90, 246 (2011) and Bakry A S, et al., *Dent Mater.*, 29, 357 (2013)—each incorporated herein by reference in its entirety. However, the available methods and agents employed for the treatment of dentin hypersensitivity have only temporary effects due to their poor efficiency both in blocking the dentinal tubules and in resisting various harsh conditions of the oral cavity for long durations. See Bakry A S, et al., *Dent Mater.*, 29, 357 (2013)—incorporated herein by reference in its entirety.

On the other hand, dental caries result from the dissolution of the enamel surfaces by the action of bacterial acids. These bacterial acids come from dental bacterial biofilms colonized on the enamel surface. See Bakry A S, et al., *Dent Mater.*, 30, 314 (2014)—incorporated herein by reference in its entirety. Loss of dental enamel tissues even in extremely small amounts cannot be compensated by dental tissues or cells because the embryonic enamel forming cells (i.e. the ameloblasts) are completely lost during the eruption of the teeth. See Bakry A S, et al., *Dent Mater.*, 30, 314 (2014)—incorporated herein by reference in its entirety. This unique developmental characteristic of the dental enamel tissue makes its repair only feasible using artificial filling materials. The most successful currently available materials used for dental enamel repair are resinous materials. These resinous materials have long un-polymerized hydrocarbon chains which can polymerize and attain significant mechanical properties upon being applied to replace the defective enamel tissues. The major chemical differences between the coronal dental tissues (enamel and dentin) and the available resinous materials used for the restoration of the lost enamel and dentin tissues leads to the inevitable failure of the interface between the resin materials and the dental tissues. Many attempts have been conducted to use materials having the same chemical composition of teeth to restore them in vitro; however, most of these attempts were difficult to be applied clinically.

The first type of bioactive glasses was introduced by Professor Larry Hench in the 1960s and was called 45S5 Bioglass. This bioactive glass has the ability to form a hydroxyapatite rich layer capable of interacting with hard and soft tissues. See Hench L L, et al., *J. Am. Ceram. Soc.*, 74, 1487 (1991)—incorporated herein by reference in its entirety. Since then, bioactive glasses have been mainly used in the field of orthopedics and periodontology. See Hench L L, et al., *J. Am. Ceram. Soc.*, 74, 1487 (1991); Hulbert S. F. et al., *Ceramics in clinical applications: Past, present, and future.*, Elsevier, Amsterdam, The Netherlands, 1987; and Yamamuro T. et al., *Handbook of Bioactive Ceramics, Vol. II: Calcium Phosphate and Hydroxylapatite Ceramics*. CRC Press, Boca Raton, Fla., 1990—each incorporated herein by reference in its entirety. Literature has focused on the use of various compositions of bioactive glasses on bone and soft tissues; however, there has been only scant information about the possible application of the bioactive glasses on enamel and dentin. See Bellucci D, et al., *Mater Sci Eng C Mater Biol Appl.*, 51, 196 (2015); Bretcanu O, et al., *J Tissue Eng Regen Med.* 3, 139 (2009); Hu S, et al., *J Mater Sci Mater Med.*, 20, 281 (2009); Stahli C, et al., *Acta Biomater.*, 19, 15 (2015); and Mao C, et al., *Biomed Mater.*, 10, 025005, (2015)—each incorporated herein by reference in its entirety. Our research team has reported excellent results using 45S5 Bioglass to restore incipient caries lesions and to remineralize subsurface demineralized lesions. 45S5 Bioglass may have further application as a potent desensitizing agent capable of treating dentin hypersensitivity symptoms by occluding the dentinal tubule orifices of dentin. See Bakry A S, et al., *J Dent*, 42, 1458 (2014); Bakry A S, et al., *J Dent Res.*, 90, 246 (2011); Bakry A S, et al., *Dent Mater.*, 30, 314 (2014); and Bakry A S, et al., *J Dent.*, 39, 599 (2011)—each incorporated herein by reference in its entirety.

In view of the foregoing, one objective of the present invention is to provide borate bioactive glass particles, and a paste that may be made from those particles and used to restore a dentin layer or an enamel layer on a surface of a tooth.

BRIEF SUMMARY OF THE INVENTION

According to a first aspect the present disclosure relates to a borate bioactive glass, which comprises
- 40-60 wt % $B_2O_3$,
- 15-25 wt % CaO,
- 15-25 wt % $Na_2O$, and
- 2-15 wt % $P_2O_5$, where each weight percentage is relative to a total weight of the borate bioactive glass.

In one embodiment, the borate bioactive glass is substantially free of $SiO_2$ or MgO.

In one embodiment, the borate bioactive glass further comprises at least one compound selected from the group consisting of $Ca(PO_3)_2$, $K_2O$, $Al_2O_3$, $TiO_2$, $CaF_2$, $Fe_2O_3$, CuO, SrO, $Bi_2O_3$, $Ce_2O_3$, $Ga_2O_3$, and ZnO.

In one embodiment, the borate bioactive glass is in the form of particles having longest dimensions of 1-200 µm.

According to a second aspect, the present disclosure relates to a borate bioactive glass paste, which comprises
- 20-60 wt % of the borate bioactive glass of the first aspect and
- 40-80 wt % phosphoric acid solution, where each weight percentage is relative to a total weight of the borate bioactive glass paste, and where the borate bioactive glass is in the form of particles.

In one embodiment, the borate bioactive glass paste further comprises a salt selected from the group consisting of $KNO_3$, NaF, $SnF_2$, $SrCl_2$, and $CaCl_2$.

In one embodiment, the borate bioactive glass paste further comprises silica particles having diameters of 1-100 µm.

In one embodiment, the borate bioactive glass paste has a bulk viscosity of 5,000-100,000 cP at 25-38 °C.

In one embodiment, the borate bioactive glass paste has a pH of 1-3, and the phosphoric acid solution is an aqueous solution of 25-85 wt % phosphoric acid relative to a total weight of the phosphoric acid solution.

In one embodiment, the borate bioactive glass paste further comprises a gelling agent.

According to a third aspect, the present disclosure relates to a method of restoring a dentin layer or an enamel layer on a surface of a tooth. The method involves
- applying the borate bioactive glass paste of the second aspect onto the surface of the tooth,
- covering the borate bioactive glass paste with a cover,
- maintaining contact between the borate bioactive glass paste and the surface of the tooth for an effective time for forming a restored dentin layer or a restored enamel layer between the borate bioactive glass paste and the surface of the tooth, and
- removing the cover and the borate bioactive glass paste.

In one embodiment, the cover is at least one selected from the group consisting of a resin, a varnish, a sealant, a bonding agent, a cement, a wax, a dental composite, a cap, a plug, a band, and a dental appliance.

In one embodiment, the cover is semipermeable.

In one embodiment, the surface of the tooth has exposed dentinal tubules.

In one embodiment, the surface of the tooth is within a dental cavity.

In one embodiment, the effective rime is 6 hours-14 days.

In one embodiment, the method further comprises contacting the cover, a second surface of the tooth, or both, with saliva or an aqueous electrolyte solution after the covering and before the removing. The aqueous electrolyte solution comprises at least one ion selected from the group consisting of
- 2-130 mmol/L sodium,
- 8-60 mmol/L potassium,
- 1-5 mmol/L calcium,
- 0.05-2.0 mmol/L magnesium,
- 5-80 mmol/L chloride,
- 20-90 mmol/L bicarbonate, and
- 1-40 mmol/L phosphate.

In one embodiment the surface of the tooth is within a mouth of a mammal.

According to a fourth aspect, the present disclosure relates to a biocompatible bone graft comprising
- the borate bioactive glass particles of the first aspect,
- a population of osteocompetent stem cells obtained from a mammalian donor, and
- a growth medium.

In one embodiment, the osteocompetent stem cells are derived from a sample of bone marrow, periosteum, dermal fibroblasts, or adipose tissue.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
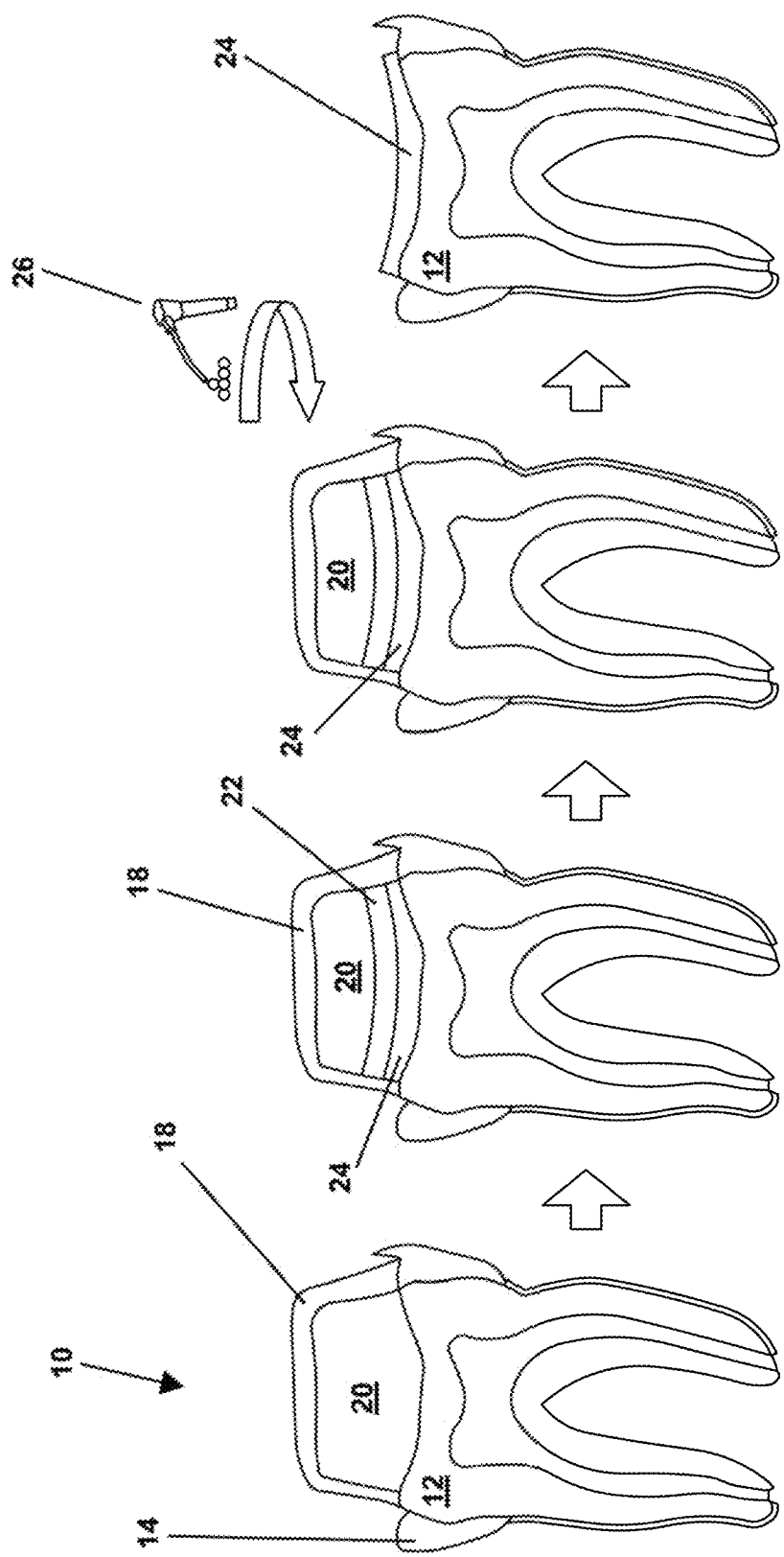
FIG. 1 is an illustration of a method for forming a restored dentin layer on the dentin surface of a tooth.

Embodiments of the present disclosure will now be described more fully hereinafter with reference to the accompanying drawings, in which some, but not all embodiments of the disclosure are shown.

The present disclosure will be better understood with reference to the following definitions. As used herein, the words "a" and "an" and the like carry the meaning of "one or more." Within the description of this disclosure, where a numerical limit or range is stated, the endpoints are included unless stated otherwise. Also, all values and subranges within a numerical limit or range are specifically included as if explicitly written out.

As used herein, "compound" is intended to refer to a chemical entity, whether as a solid, liquid, or gas, and whether in a crude mixture or isolated and purified.

As used herein, a "composite" is intended to refer to a solid material comprising more than one phase, structure, and/or compound. As used herein, the term "bioactive" denotes a material that generates a positive reaction when in a certain biological environment and/or is subjected to a chemical or physical process that modifies the material's surface so as to form a substrate that is favorable for the remineralization of dentin or enamel, or the re-growth of bone tissue. A bioactive material may bind chemically with the surrounding bone or promote cell attachment or growth.

As used herein, the term "glass" refers to a non-crystalline amorphous solid having a breaking stress or surface compressive stress of 10 MPa-30 GPa at 20-40° C. Glass may or may not comprise silica ($SiO_2$).

According to a first aspect, the present disclosure relates to a borate bioactive glass, which comprises 40-60 wt %, preferably 42-55 wt %, more preferably 44-50 wt % $B_2O_3$ (borate); 15-25 wt %, preferably 17-24 wt %, more preferably 18-23 wt % CaO; 15-25 wt %, preferably 17-24 wt %, more preferably 18-23 wt % $Na_2O$; and 2-15 wt %, preferably 3-10 wt %, more preferably 4-8 wt % $P_2O_5$, where each weight percentage is relative to a total weight of the borate bioactive glass. The borate bioactive glass may have a Ca:P molar ratio of 1:1-17:1, preferably 2:1-10:1, more preferably 3:1-7:1.

The borate bioactive glass may be made by melting glass precursors such as carbonate salts, a phosphate salt, and boric acid ($H_3BO_4$) to form a glass. This method may be known as a "melt quench" synthesis. For example, the glass precursors $Na_2CO_3$, $CaCO_3$, $H_3BO_4$, $NaH_2PO_4$, as well as others as needed, may be ground into powders using a mortar and pestle, or obtained as powders, and mixed. These powders may comprise particles having largest dimensions of 0.1-200 μm, preferably 0.5-100 μm, more preferably 1-50 μm. Preferably the mixed powder contains a ratio of the glass precursors to generate an equivalent weight percent as mentioned in the first aspect. For instance, the mixed powder may contain the glass precursors in relative amounts in order to provide an overall elemental composition of 11-14 mol % Na, 6.2-8.2 mol % Ca, 0.4-2.4 mol % P, 23.5-25.5 mol % B, and 52.9-54.9 mol % O. In other embodiments, different glass precursors may be used to ultimately produce equivalent compositions after melting to form a glass. For instance, $Na_2B_4O_7$ may be used in place of $H_3BO_4$, or $Na_2HPO_4$ may be used in place of $NaH_2PO_4$. A person having ordinary skill in the art may be able to determine a practical amount of glass precursors to form a glass having one of the aforementioned compositions.

In one embodiment, the powder mixture of glass precursors may be heated in a furnace, oven, or kiln for 0.5-3 h, preferably 0.6-2 h, more preferably 0.8-1.2 h at a temperature of 1100-1600° C., preferably 1250-1550° C., more preferably 1400-1500° C. Preferably the powder mixture is heated in air. In one embodiment, the glass precursors may be heated in a Pt or Pt alloy crucible. The heated mixture may be allowed to cool to room temperature, or may be poured as a molten glass onto a flat surface for cooling or poured into a mold. In one embodiment, the molten glass may be poured onto a steel plate and further spread or pressed to decrease the thickness of the poured layer, for example, to a thickness of 0.1-10 mm, preferably 0.2-5 mm, more preferably 0.2-1 mm. A cooled glass may then be crushed or ground to produce borate bioactive glass in the form of particles. This crushing or grinding may be done with a mortar and pestle, a grinding mill, a file, a glass crusher, or a sander.

In one embodiment, a sol-gel method may be used to form the borate bioactive glass at lower temperatures and in the form of particles. This involves the creation of a solution (sol), which is composed of dissolvable glass precursors in an aqueous solvent, such as an acid. A gel is then formed through hydrolysis and condensation reactions, and the gel is heated for drying, oxide formation, and removal of organic compounds. Because of the lower fabrication temperatures used in this method, there is a greater level of control on the composition and homogeneity of the product. In addition, glass particles formed this way have higher porosity, which leads to a greater surface area. This may enhance remineralization on a tooth surface. A variation of a sol-gel method may involve forming a sol which is then sonicated and irradiated with microwave radiation to produce a precipitate.

The precipitate may then be dried and calcined at 600-800° C. to produce the borate bioactive glass in the form of particles.

In an alternative embodiment, particles from different glass powders may be mixed and re-melted to form the glass. For example, a powder from a glass containing $Na_2O$ and $P_2O_5$ may be mixed with a second powder from a glass containing CaO and $B_2O_3$.

In one embodiment, the borate bioactive glass further comprises $Ca(PO_3)_2$, $K_2O$, $Al_2O_3$, $TiO_2$, $CaF_2$, $Fe_2O_3$, CuO, SrO, $Bi_2O_3$, $Ce_2O_3$, $Ga_2O_3$, and/or ZnO, preferably $TiO_2$, $CaF_2$, $Fe_2O_3$, CuO, SrO, and/or ZnO, more preferably $TiO_2$, SrO, and/or ZnO. Preferably, these compounds or precursors to these compounds are added to the powder mixture before the heating and melting. In one embodiment, one or more of $Ca(PO_3)_2$, $K_2O$, $Al_2O_3$, $TiO_2$, $CaF_2$, $Fe_2O_3$, CuO, SrO, $Bi_2O_3$, $Ce_2O_3$, $Ga_2O_3$, and/or ZnO may be present in the borate bioactive glass, each at a weight percentage of 0.5-25 wt %, preferably 1-20 wt %, more preferably 2-15 wt %, even more preferably 3-10 wt %, relative to a total weight of the borate bioactive glass particles.

In one embodiment, the borate bioactive glass is substantially free of $SiO_2$ or MgO. The term "substantially free of $SiO_2$ or MgO" refers to the condition in which the $SiO_2$ content, the MgO content, or both are less than 0.5 wt %, preferably less than 0.2 wt %, more preferably less than 0.1 wt % with respect to the total weight of the borate bioactive glass. Preferably, in terms of elemental compositions on the basis of the total moles of each element, the borate bioactive glass being "substantially free of $SiO_2$ or MgO" also means that Si, Mg, or both are present at less than 0.2 mol %, preferably less than 0.1 mol %. In some embodiments, borate bioactive glass completely free of Si or Mg may not be possible due to sample impurities or environmental contamination.

In an alternative embodiment, $SiO_2$ and/or MgO may be present in the borate bioactive glass at a weight percentage of 0.5-25 wt %, preferably 1-20 wt %, more preferably 2-15 wt %, even more preferably 3-10 wt %, relative to a total weight of the borate bioactive glass. A borate bioactive glass comprising both $SiO_2$ and $B_2O_3$ may be considered as a type of borosilicate glass.

As mentioned earlier, in one embodiment, the borate bioactive glass has $B_2O_3$ present at a weight percentage of 40-60 wt % relative to a total weight of the borate bioactive bioglass. This may be a higher $B_2O_3$ wt % than other borate-containing bioactive glasses. The amount of borate may enable a faster demineralization of the borate bioactive glass, as will be discussed later in more detail.

Borate bioactive glass particles may have overall shapes that are spherical, ellipsoidal, oblong, ovoidal, angular, rectangular, prismoidal, or some other shape. The borate bioactive glass particles may very likely have sharp, acute, pointed, or jagged edges. In one embodiment, the borate bioactive glass particles have longest dimensions or diameters of 1-200 µm, preferably 2-100 µm, more preferably 5-40 µm. In one embodiment, borate bioactive glass particles on the smaller side, such as those having diameters of 1-5 µm or 1-3 µm, may be used to facilitate mixing and/or to more quickly dissolve in the phosphoric acid solution. In other embodiments, the borate bioactive glass particles may have submicron diameters, such as 100-900 nm, preferably 200-800 nm. As the average diameter of dentinal tubules is about 1 µm, particles with submicron diameters may be able to enter a dentinal tubule. The ratio of the longest dimension to the shortest dimension of the borate bioactive glass particles may be 1:1-1:10, preferably 1:1.05-1:5, more preferably 1:1.1-1:2. In one embodiment, the borate bioactive glass particles have longest dimensions within 75-125% of the average particle longest dimension, preferably within 80-120%. In one embodiment, the borate bioactive glass particles may have surface area to volume ratios of 15 $nm^{-1}$-50 $µm^{-1}$, preferably 0.3 $µm^{-1}$-10 $µm^{-1}$ more preferably 0.8 $µm^{-1}$-5 $µm^{-1}$ and bulk densities of 1-8 $g/cm^3$, preferably 1.2-5 $g/cm^3$, more preferably 1.5-4 $g/cm^3$. In some embodiments, the borate bioactive glass particles may have pores with diameters of 1-12 nm, preferably 1.5-8 nm, more preferably 1.8-5 nm, which may provide higher surface area to volume ratios.

In an alternative embodiment, the borate bioactive glass particles may comprise particles clustered together as agglomerates. As used herein, the term "agglomerates" refers to a clustered particulate composition comprising primary particles, the primary particles being aggregated together in such a way so as to form clusters thereof, with at least 50 volume percent of the clusters having a mean diameter or longest dimension that is at least 2 times the mean diameter or longest dimension of the primary particles, and preferably at least 90 volume percent of the clusters having a. mean diameter or longest dimension that is at least 5 times the mean diameter or longest dimension of the primary particles. The primary particles of an agglomerate may be the borate bioactive glass particles having sizes as described above, or having smaller mean diameters or longest dimensions such as 100-800 nm, preferably 200-700 nm. Agglomerates may be formed by partially re-melting borate bioactive glass particles or by forming the borate bioactive glass in a different way, such as by flame pyrolysis. In other embodiments, a borate bioactive glass may be formed into a glass wool having fiber threads with diameters of 0.3-12 µm, preferably 1-10 µm, more preferably 2-8 µm.

According to a second aspect, the present disclosure relates to a borate bioactive, glass paste, which comprises 20-60 wt %, preferably 25-55 wt %, more preferably 28-40 wt % of the borate bioactive glass particles and 40-80 wt %, preferably 50-75 wt %, more preferably 60-70 wt % phosphoric acid solution, where each weight percentage is relative to a total weight of the borate bioactive glass paste. This borate bioactive glass paste may also be referred to as a gel, composite, glue, or putty. The phosphoric acid solution is a mixture of water and phosphoric acid, where the phosphoric acid is present at 25-85 wt %, preferably 40-70 wt %, more preferably 45-55 wt % in relation to the total weight of the phosphoric acid solution.

In an alternative embodiment, a different source of phosphorus may be used in place of the phosphoric acid solution. For example, hypophosphorous acid, hypophosphoric acid, phosphorous acid, pyrophosphoric acid, triphosphoric acid, ammonium dihydrogen phosphate, trimethyl phosphafate, Methyl phosphate (TEP), disodium hydrogen phosphate, monosodium phosphate, sodium tripolyphosphate, sodium hexametaphosphate, or phosphorous pentoxide may be used having a weight percentage of phosphorus equivalent to the phosphoric acid solution, or having a weight percentage of phosphorus within 25%, preferably within 15% of that within the phosphoric acid solution. In this alternative embodiment, other inorganic acids, such as HCl, $HNO_3$, or $H_2SO_4$ may be added to the solution to provide an acidity similar to a 30-60 wt % phosphoric acid solution.

The water may be tap water, distilled water, bidistilled water, deionized water, deionized distilled water, reverse osmosis water, and/or some other water. In one embodiment, the water is bidistilled to eliminate trace metals. Preferably the water is bidistilled, deionized, deinonized distilled, or reverse osmosis water and at 22-27° C. has a conductivity of less than 10 $µS·cm^{-1}$, preferably less than 1 $µS·cm^{-1}$, a resistivity greater than 0.1 MΩ·cm, preferably greater than 1 MΩ·cm, more preferably greater than 10 MΩ·cm, a total solid concentration less than 5 mg/kg, preferably less than 1 mg/kg, and a total organic carbon concentration less than 1000 µg/L, preferably less than 200 µg/L, more preferably less than 50 µg/L.

Preferably the borate bioactive glass paste is formed by bringing into contact the borate bioactive glass particles with the phosphoric acid solution. The borate bioactive glass particles may be stirred, mixed, inverted, or otherwise agitated to contact each borate bioactive glass particle with phosphoric acid. In one embodiment, the paste maintains a homogenous dispersion of borate bioactive glass particles. However, in another embodiment, the borate bioactive glass particles may settle out of the phosphoric acid solution, for example by sinking to the bottom of a container holding the borate bioactive glass paste.

In one embodiment, the borate bioactive glass paste further comprises a salt such as $KNO_3$, NaF, $SnF_2$, $SrCl_2$, and/or $CaCl_2$, preferably NaF, $SnF_2$, and/or $CaCl_2$, more preferably NaF and/or $SnF_2$. These salts may provide beneficial effects to dentin and enamel remineralization; for instance, fluoride from NaF or $SnF_2$ may intercalate and strengthen a hydroxyapatite lattice within or on an enamel or dentin layer. The salt may be present at a weight percentage of 0.1-10 wt %, preferably 0.2-5 wt %, more preferably 0.25-4 wt % relative to a total weight of the borate bioactive glass paste.

In one embodiment, the borate bioactive glass paste further comprises silica particles having diameters of 1-100 µm, preferably 5-80 µm, more preferably 10-75 µm. However, in other embodiments, the silica particles may be much smaller, such as having diameters of 4-100 nm, preferably 5-50 nm. Silica particles may be present at a weight percentage of 1-50 wt %, preferably 2-20 wt %, more preferably 3-10 wt % relative to a total weight of the borate bioactive glass paste. Alternatively, in other embodiments, particles of other glass materials may be used such as soda-lime glass, borophosphosilicate glass, flint glass, chalcogenide glass, fluorozirconate glass, fluoroaluminate glass, or fluorosilicate glass. In a preferred embodiment, there is no chemical interaction between silica particles (or other particles) and borate bioactive glass particles in the borate bioactive glass paste. For instance, in a borate bioactive glass paste comprising silica particles, the borate bioactive glass particles do not become doped by Si, and thus remain substantially free of $SiO_2$. In one embodiment, these silica or other particles may be present in the borate bioactive glass paste in order to modify the overall chemical composition of the borate bioactive glass paste, or to change its physical properties, such as viscosity or density.

In one embodiment, the borate bioactive glass paste has a bulk viscosity of 5,000-100,000 cP, preferably 10,000-90,000 cp, more preferably 20,000-80,000 cp at 25-38° C. The borate bioactive glass paste may also be considered as a gel, a putty, or a non-Newtonian fluid such as a Bingham plastic, a dilatant, or a pseudoplastic. The borate bioactive glass paste may have viscoplastic properties similar to a jelly food product, mayonnaise, mud, a slurry, or toothpaste. In another embodiment, the borate bioactive glass paste may be a clumped mass of solids, similar to wet sand. In alternative embodiments, the bulk viscosity may be higher than 100,000 cP, such as 120,000-250,000 cP, preferably 150,000-200,000 cP.

In one embodiment, the borate bioactive glass paste has a pH of 1-3, preferably 1.2-2.8, more preferably 1.5-2.5. In an alternative embodiment, the borate bioactive glass paste may have a higher pH while still being considered acidic, such as a pH of 3.0-6.8, preferably 3.5-6.0, more preferably 4.0-5.5. In other alternative embodiments, the borate bioactive glass paste may not contain an acid (or may have contained an acid, such as phosphoric acid, which is neutralized with a base), and may have a more neutral pH of 6.8-7.7, preferably 6.9-7.4. In other embodiments, the borate bioactive glass paste may have a pH that is lower than 1. In some embodiments, a pH of the borate bioactive glass paste may rise over time. For instance, a borate bioactive glass paste just mixed may have a pH of about 0, and after 0.5-1 h, the pH may rise to about 2.0 due to demineralization of the borate bioactive glass.

In one embodiment, the borate bioactive glass paste further comprises a gelling agent. As defined herein, a gelling agent is a compound that when mixed with a fluid or semifluid increases the viscosity of the fluid or semifluid. The gelling agent may be an acid stable polymer, such as xantham polymer, polybenzimidazole, polyacrylic acid, high density polyethylene (HDPE), or polytetrafluoroethylene (PTFE). Alternatively, the gelling agent may be an inorganic compound such as talc, a layered double hydroxide, boron carbide ($B_4C$), silicon carbide (SiC), zirconia, or some other ceramic or glass-ceramic. In certain embodiments, the gelling agent may be a biodegradable polymer such as poly lactic-co-glycolic acid, poly lactic acid, poly glycolic acid, polyanhydride, poly(ortho)ester, polyurethane, poly(butyric acid), poly(valeric acid), polycaprolactone, poly(lactide-co-caprolactone), or poly(trimethylene carbonate). In other embodiments, these materials may be added not necessarily to increase the viscosity of the borate bioactive glass paste, but to allow a lower concentration of borate bioactive glass particles in the paste while maintaining a similar viscosity, density, or other physical properties. A gelling agent may be present at a weight percentage of 0.1-20 wt %, preferably 1-15 wt %, more preferably 2-10 wt % relative to a total weight of the borate bioactive glass paste. Silica particles, as previously mentioned, may also be considered gelling agents.

According to a third aspect, the present disclosure relates to a method of restoring a dentin layer or an enamel layer on a surface of a tooth. The method involves applying the borate bioactive glass paste of the second aspect onto the surface of the tooth. Then, the borate bioactive glass paste is covered with a cover, and contact between the borate bioactive glass paste and the surface of the tooth is maintained for an effective time to form a restored dentin layer or a restored enamel layer between the borate bioactive glass paste and the surface of the tooth. Next, the cover and the borate bioactive glass paste may be removed, leaving behind a restored dentin or enamel layer.

The borate bioactive glass paste may be applied to a location of a tooth having an eroded or removed enamel and/or dentin layer, or having an early erosion lesion, which may be caused by chemical erosion, such as exposure to acidic compounds, beverages, or foods, or may be caused by physical abrasion, such as by filing or grinding. In one embodiment, this location to receive the borate bioactive glass paste may have exposed dentinal tubules. In another embodiment, an enamel and/or dentin layer may be removed by a physical impact against a tooth, which may result in a chipped tooth. Similarly, a physical impact may result in a cracked tooth having a fissure with exposed dentinal tubules. In another embodiment, the location may be within or on a cavity or depression caused by tooth decay (i.e. dental caries). In another embodiment, the location may be located below the gum line or at a place where the gum has receded. Alternatively, the borate bioactive glass paste may be applied to a surface of a tooth that is not enamel or dentin, for example, the cementum. As non-limiting examples, the tooth may be an incisor, a cuspid, a bicuspid, a premolar, or a molar, and may be a primary tooth or a permanent tooth. The borate bioactive glass paste may be placed by means of a dental spatula, an elevator, an applicator, or a brush, or may be applied by extruding from a tube or syringe. In one embodiment, where the borate bioactive glass paste is applied by an applicator, it may be applied by a Microbrush applicator. In one embodiment, the borate bioactive glass paste may be applied to just fill a cavity or depression on the surface of the tooth, so that the borate bioactive glass paste lies flush against the surface of the tooth. In other embodiments, an amount of borate bioactive glass paste may be applied that is less than that required for a flush surface (thus leaving a concave surface or a surface within the tooth), or the amount of borate bioactive glass paste may be greater than that required for a flush surface (thus leaving a convex shape). The ratio of the applied volume of the borate bioactive glass paste to the volume of the tooth above the gum line may be 1:200-1:1, preferably 1:50-1:2, more preferably 1:40-1:5. In an alternative embodiment, a single volume of borate bioactive glass paste may not be placed just on a single tooth, but on two or more teeth as a contiguous volume, such as filling a gap between two teeth.

In one embodiment, the borate bioactive glass paste may be formed immediately before applying onto a tooth, for example, the borate bioactive glass particles may be contacted with the phosphoric acid solution no more than 20 minutes, preferably no more than 10 minutes before the applying. In other embodiments, the borate bioactive glass paste may be formed in advance and then stored for 1-12 months, preferably 2-8 months, more preferably 3-6 months in an airtight container and stored at room temperature, or in a refrigerator or freezer. In another embodiment, a mixture of the borate bioactive glass particles and water may be formed in advance and stored, and then within 20 minutes or 10 minutes of application to a tooth, the mixture may be mixed with concentrated phosphoric acid to form the borate bioactive glass paste.

In one embodiment, before applying the borate bioactive glass paste, the surface of the tooth may be cleaned or prepared by air jet, water jet, polishing, brushing, drilling, scraping, grinding, acid etching, or demineralizing. Acid etching or demineralizing may be done with a solution comprising citric acid, phosphoric acid, EDTA, hydrochloric acid, acetic acid, or some other inorganic acid, organic acid, or chelating agent. In one embodiment, preparation of the surface by drilling, scraping, grinding, acid etching, or demineralizing may increase the surface roughness and provide additional crevices for a layer of calcium phosphate to deposit and anchor. The surface roughness on the prepared tooth, for example, within a 10 µm×10 µm region, may possess an Ra roughness value of 0.10-0.30 µm, preferably 0.12-0.25 µm. However, in some embodiments, a tooth may already have an equivalent surface roughness by erosion and may not need additional abrasion or etching.

In one embodiment, the cover is at least one selected from the group consisting of a resin, a varnish, a sealant, a bonding agent, a cement, a wax, a dental composite, a cap, a plug, a band, and a dental appliance. The cover may be formed by a glass ionomer cement, a resin modified glass ionomer cement, a poly acid modified composite resin, a composite resin, a compomer, a dental porcelain, a ceramic-resin hybrid, a metal or metal amalgam, a zinc oxide cement, a polycarboxylate cement, or zinc oxide eugenol.

Preferably the cover is made of a biocompatible material. As defined here, a biocompatible material is one that does not produce a toxic, injurious, or immunological response when in physical contact with a living cell or tissue, especially with a tooth or tissues within an oral cavity. Biocompatible polymers that may be present in the cover include, but are not limited to a fluoropolymer, a polyarylether ketone, a polyether, a polyester, a polyamide, a polyimide, a polyurethane, a polycarbonate, a polyanhydride, a polyurea, a polyolefin, a polystyrene, a polysulfone, a polysulfide, a polyketone, a poly(methyl acrylate), a polymethacrylamide, a vinyl polymer, and a polysiloxane. The cover may have a thickness of 0.05-2 mm, preferably 0.07-1 mm, more preferably 0.1-0.5 mm, and an exterior surface area of 1-280 mm$^2$, preferably 2-100 mm$^2$, more preferably 3-50 mm$^2$. In one embodiment, the cover is acid resistant or acid stable. In another embodiment, a part of the cover in contact with the borate bioactive glass paste may react. In this embodiment, a precipitate may form on that part of the cover, or the cover may be passivated by the reaction.

In one embodiment, a resin, varnish, sealant, bonding agent, cement, wax, or dental composite may be applied to the tooth as a liquid, viscous gel, or paste, and may then harden and/or adhere to the tooth over a period of time or may be light cured, for instance, with a light having a maximum emission wavelength of 450-470 nm. In alternative embodiments, the cover may be cured by applying heat, or may be applied at a hot temperature and then cured or hardened by cooling to the surrounding temperature. A resin, varnish, sealant, bonding agent, cement, wax, or dental composite may self-cure by exposure to air or by being mixed or exposed to some other reactive ingredient. In a preferred embodiment, the cover is a layer of a bonding agent, such as Clearfil SE Bond (Kuraray), Adper Single Bond Plus (3M), Adper Scotchbond SE (3M), XENO V (Dentsply), Adper Easy Bond (3M) and may be light cured. The exterior surface area of a cover comprising a resin, varnish, sealant, bonding agent, cement, wax, or dental composite may be 0.5-99%, preferably 1-60%, more preferably 2-20% of the total exposed surface area of the tooth without the cover, and the cover may have a shear bond strength of 15-50 MPa, preferably 20-45 MPa, more preferably 25-37 MPa.

In an alternative embodiment, a compound such as a particular resin, bonding agent, cement, or dental composite may be mixed into the borate bioactive glass paste before the applying. After the applying, only an exterior layer of the borate bioactive glass paste may be hardened or cured, without affecting the interior volume of the paste. In this alternative embodiment, a cover may not be required.

In one embodiment, the cover may be a layer of two or more materials. For instance, a first layer may be placed in contact with the borate bioactive glass paste on a tooth, and this first layer may provide acid resistance against the borate bioactive glass paste. A second layer may provide additional strength. In another embodiment, a cover of two or more layered materials may be used where a compound of the first layer reacts with a compound of the second layer to harden or adhere the combined layers. For instance, the first layer may be a resin, and the second layer may be a hardening agent or a cross-linking agent. In a related embodiment, an adhesive may be applied around the location of the borate bioactive glass paste on a tooth, such as along the perimeter of the borate bioactive glass paste placed on a tooth. Then, a flexible material may be placed over and adhered with the adhesive, thus sealing the borate bioactive glass paste on the tooth.

In one embodiment, the cover may be provided by a removable dental appliance which does not adhere to a tooth but is instead held by frictional coupling with one or more teeth. The removable dental appliance may be similar to a mouth guard or a retainer. In one embodiment, the cover may fit over a tooth as a cap or the cover may be a band that encircles a tooth. A cap or a band may be made of an elastomeric material, such as nitrile, silicone, or styrene butadiene. In another embodiment, a depression or cavity may only be partially filled with the borate bioactive glass paste, to leave a volume that is filled by the cover. In this sense, the cover may be considered a plug. A cover in the form of a cap, band, or plug may be held in place by adhesion to the tooth, by frictional coupling to the tooth, or by a combination of both. In one embodiment, a dental wax or orthodontic wax comprising paraffin may be used, or some other wax such as carnauba wax or beeswax.

In one embodiment, the cover may be semipermeable, meaning that certain molecules or ions may pass through the cover by passive diffusion. For instance, chloride ions may exist at a concentration of 25-35 mmol/L in a bulk solution on the side of the cover opposite the borate bioactive glass paste. Over a time span of 20-30 hours, the concentration of chloride ions in the borate bioactive glass paste may increase from a negligible concentration to a concentration of 5-15 mmol/L, as a result of passive diffusion of the chloride ions through the cover. A semipermeable cover may be traversed by pores or channels to allow certain ions or molecules to diffuse, and a person having ordinary skill in the art may adjust the chemical and physical properties of a cover in order to control its permeability. Where the cover is semipermeable, preferably any diffusion from the borate bioactive glass paste is not injurious to the patient. However, in other embodiments, the cover is impermeable.

With the borate bioactive glass paste in contact with the surface of a tooth and covered with a cover, the borate bioactive glass paste and the surface of the tooth may be maintained in contact for an effective time to form a restored dentin layer and/or a restored enamel layer at the interface of the borate bioactive glass paste and the surface of the tooth. The restored dentin and/or restored enamel layer may be called an "interaction layer." In one embodiment, this effective time may be 6 h-14 days, preferably 12 h-9 days, more preferably 5 days-8 days. The restored dentin layer or the restored enamel layer may have a thickness of 30 µm-1.5 mm, preferably 50 µm-1 mm, more preferably 80 µm-500 µm.

In an alternative embodiment, the effective time may be shorter than 6 h, for example, 20-60 min for the purpose of forming a restored layer of a smaller thickness, for example, 5-15 µm. In this alternative embodiment where the effective time is about an hour or less, the cover may not be necessary. In some embodiments, the borate bioactive glass paste may be simultaneously applied to both enamel and dentin surfaces of a tooth, and may form both restored enamel and restored dentin layers.

Figure 4A:
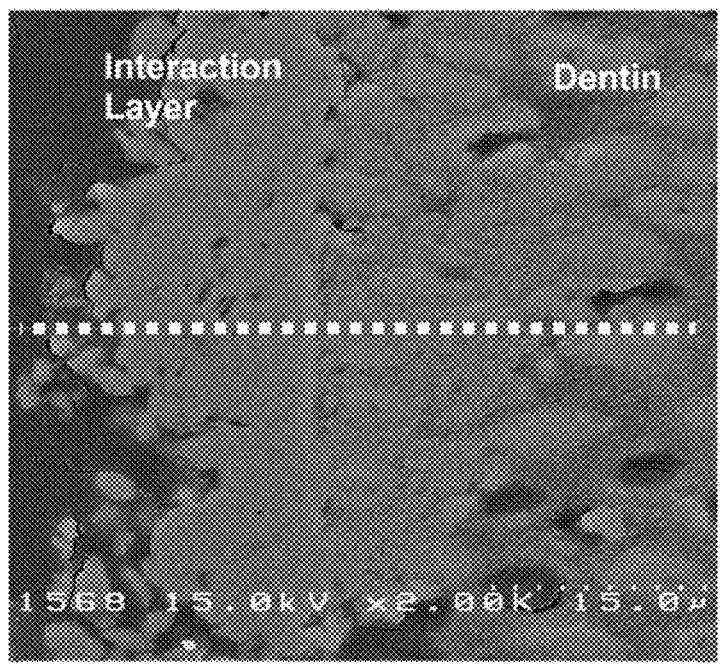
FIG. 4A is an FE-SEM image of a tooth cross-section having an interaction layer of calcium phosphate deposited on the dentin surface.
Figure 4B:
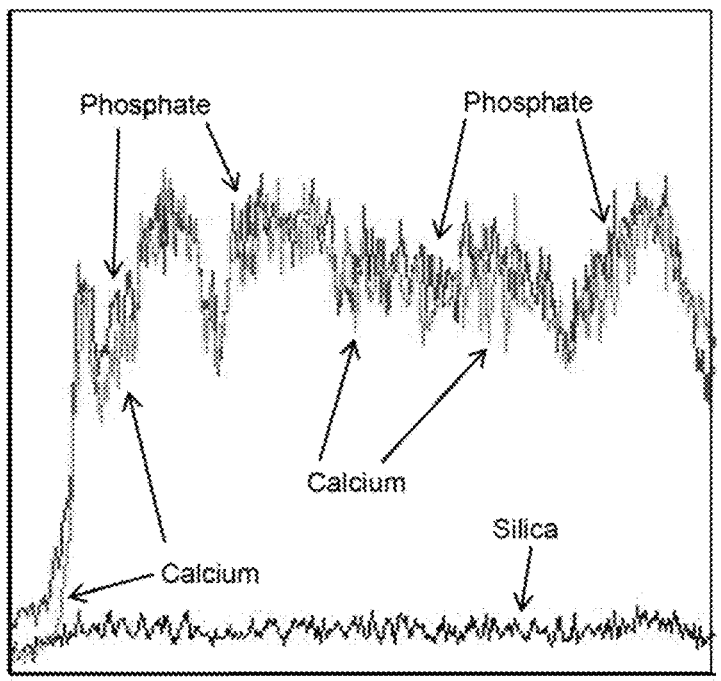
FIG. 4B is an EDS line scan profile corresponding with the dotted line on the tooth cross-section in FIG. 4A.
Figure 7:
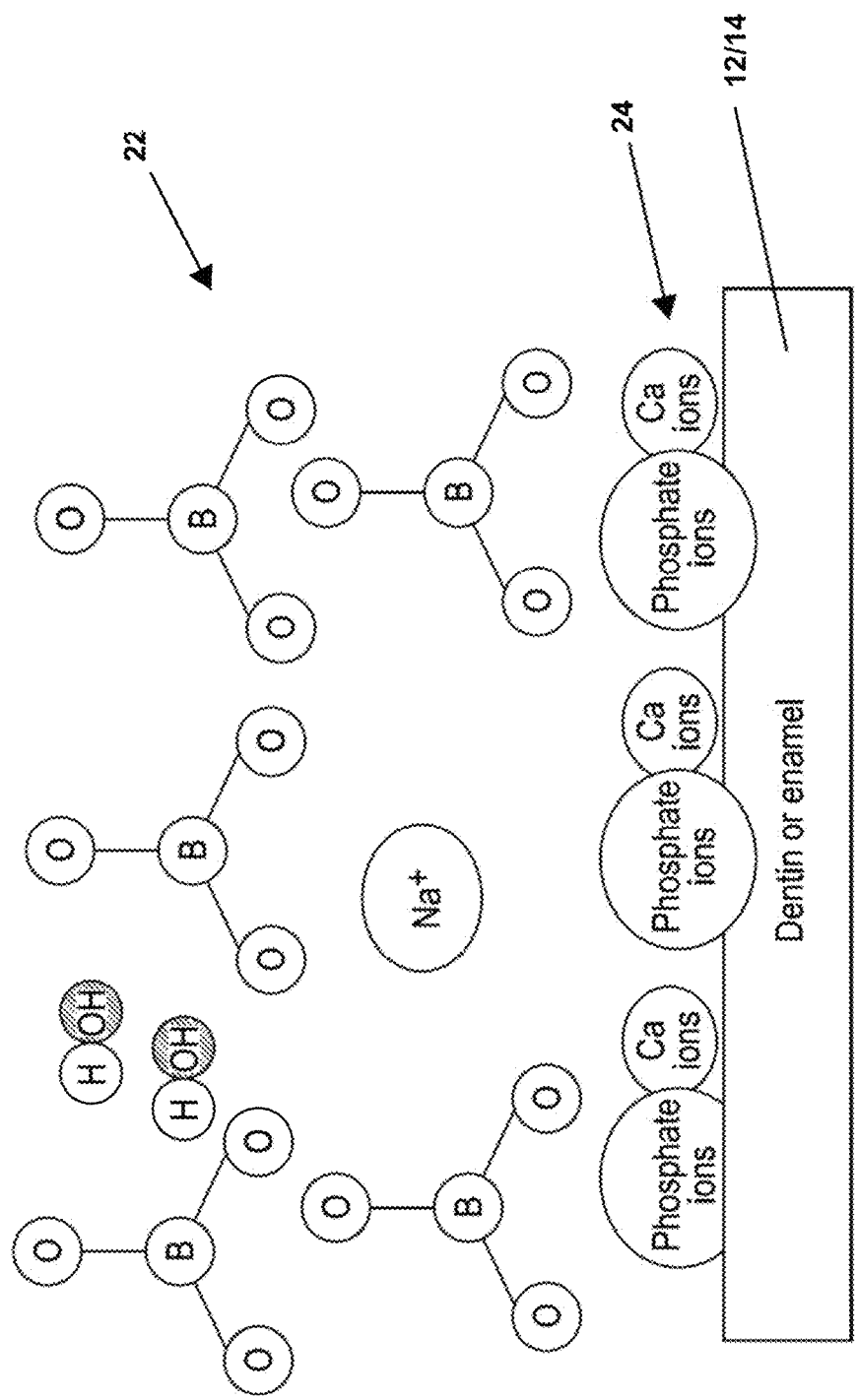
FIG. 7 is a diagram showing a fully degraded borate bioactive glass paste into soluble compounds and a layer of calcium phosphates deposited on an enamel or dentin surface.

In one embodiment, the restored dentin or enamel layer results from the precipitation or mineral deposition of calcium, phosphate, and other minerals from the borate bioactive glass paste or borate bioactive glass particles. In one embodiment, 50-98 wt %, preferably 60-95 wt %, more preferably 70-90 wt % of the original weight of the borate bioactive glass particles degrades into calcium phosphates and soluble compounds, such as sodium and borate, as shown in FIG. 7. The restored dentin or enamel layer may comprise calcium phosphates at a wt % of 50-99.9 wt %, preferably 70-98 wt %, more preferably 75-95 wt %, relative to a total weight of the restored dentin or enamel layer. The calcium phosphates present in the restored dentin or enamel layer may be in the form of monocalcium phosphate, dicalcium phosphate, tricalcium phosphate, octacalcium phosphate, amorphous calcium phosphate, dicalcium diphosphate, and/or calcium triphosphate. The calcium phosphates may also contain compounds like hydroxyapatite, apatite, and/or tetracalcium phosphate. Preferably 65-99.5 mol %, more preferably 80-95 mol % of the calcium phosphates in contact with the tooth surface form chemical bonds with the tooth surface. The restored dentin or enamel layer may further comprise other compounds from the borate bioactive glass paste, such as boron or sodium, or other additives as previously mentioned such as aluminum, fluoride, zinc, iron, or bismuth. A restored dentin layer may have an equivalent composition as a restored enamel layer, and either may have similar calcium phosphate concentrations as the original dentin or enamel surface. For example, FIGS. 4A and 4B show a tooth cross-section with EDS line scan spanning both an interaction layer and the original dentin layer of the tooth. The amounts of calcium detected across the two layers do not vary dramatically, and the same can be said about the amounts of phosphate across the two layers. Both layers show negligible amounts of silica.

Figure 5:
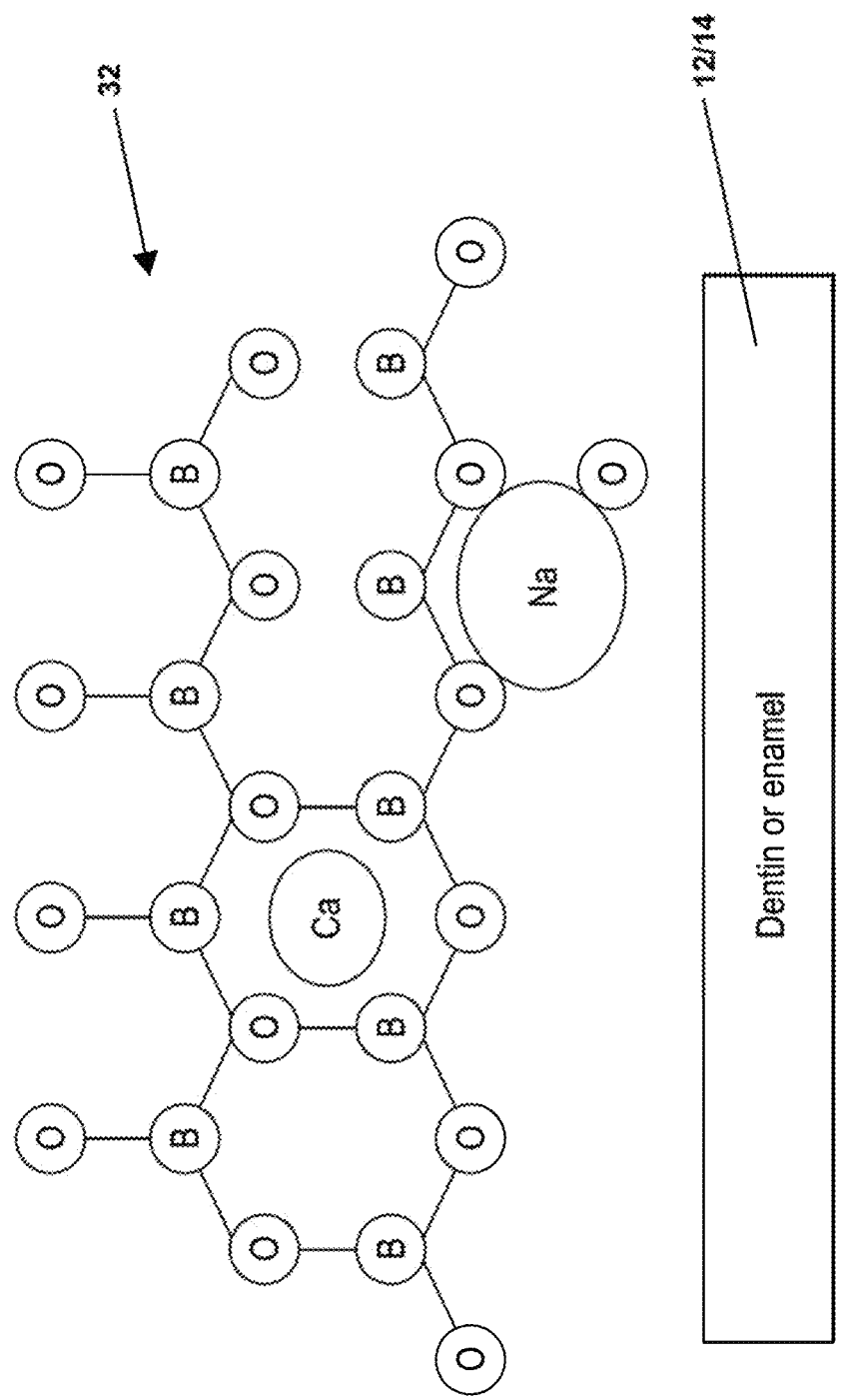
FIG. 5 is a diagram showing a borate bioactive glass particle near a dentin or enamel surface.
Figure 6:
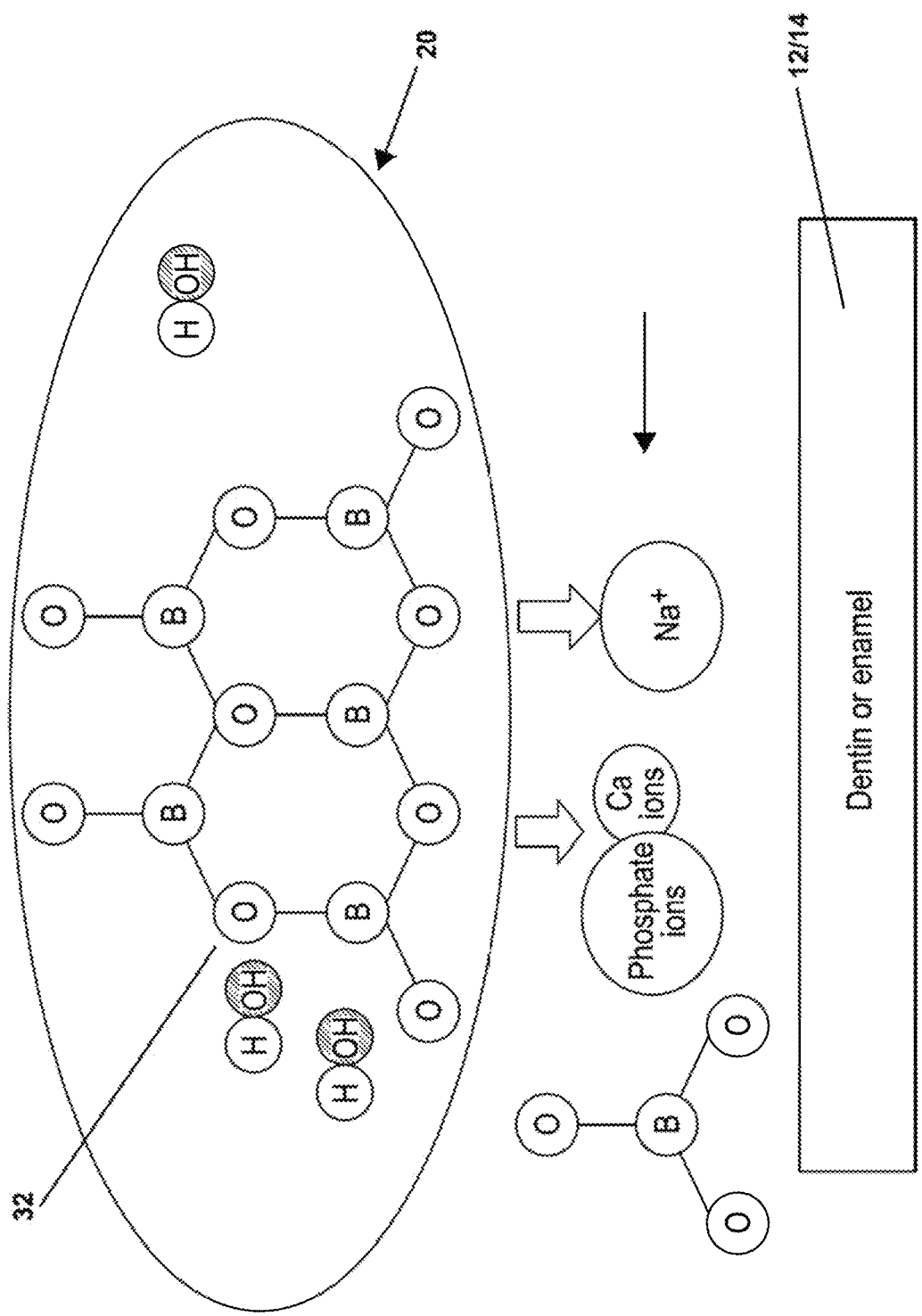
FIG. 6 is a diagram showing the degradation of borate bioactive glass paste into calcium phosphates and soluble compounds.

FIGS. 5-7 show the progression of borate bioactive glass paste depositing a calcium phosphate layer on the dentin or enamel surface 12/14 of a tooth. FIG. 5 shows a structure of a borate bioactive glass particle 32 having calcium and sodium ions and in proximity of a dentin or enamel surface 12/14. FIG. 6 shows that the borate bioactive glass particle 32 within the borate bioactive glass paste 20 releases calcium, phosphate, sodium, and borate ions. The calcium ions and phosphate ions deposit as a layer of calcium phosphates 24 on the dentin or enamel surface 12/14. FIG. 7 shows the continued dissolution and demineralization of the borate bioactive glass particle into soluble compounds 22, while the calcium phosphate layer 24 is maintained.

Following the effective time to form a restored dentin or enamel layer, the cover and remaining borate bioactive glass paste and/or soluble compounds may be removed. The removing may be done by an air jet, a water jet, or a dental tool such as an excavator, an explorer, forceps, a pick, a curette, a scaler, a probe, an aspirator, a brush, a file, or a polisher. Preferably, after a tool is used for the removing, the restored dentin or enamel layer is rinsed with water.

In one embodiment, the restored dentin or enamel layer may be polished to remove irregularities. In another embodiment, the restored dentin or enamel layer may be covered with a dental composite, sealant, or varnish. In another embodiment, the mouth of a patient having a restored dentin or enamel layer may be rinsed with a fluoride-containing solution, such as a mouthwash having 0.010-0.025 wt % sodium fluoride relative to a total weight of the mouthwash. In another embodiment, a second application of borate bioactive glass paste may be applied to a restored dentin or enamel layer. Here, the multiple applications may be used to build up a thicker calcium phosphate layer than would be possible with one application, and may be used in deep caries. In one embodiment, a second application may use a borate bioactive glass paste having a different composition than a first application. For example, a first application may use a composition to deposit a calcium phosphate layer having large pores, and a second application may use a composition chosen to deposit calcium phosphate within those large pores, in order to further strengthen the calcium phosphate layer. In other embodiments, a second application or more of borate bioactive glass paste may depend on the condition of the restored dentin or enamel layer. Preferably, a dentist or dental professional having ordinary skill in the art may be able to determine an advantageous composition of borate bioactive glass paste to use, an effective contacting time, and whether or not additional applications are needed. In one embodiment, a restored dentin or enamel layer may be maintained indefinitely with proper oral hygiene.

Figure 2:
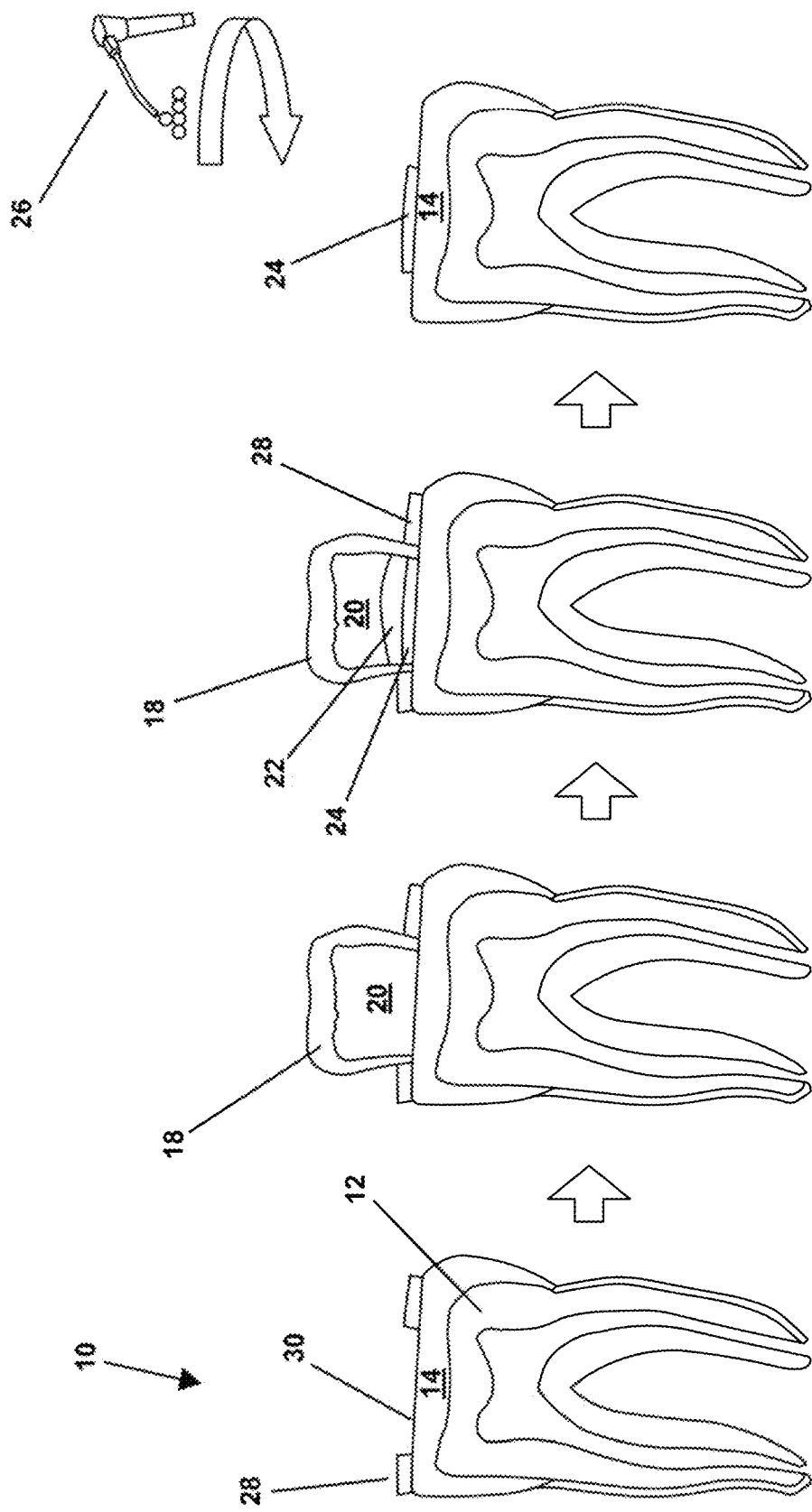
FIG. 2 is an illustration of a method for forming a restored enamel layer on the enamel surface of a tooth.

FIGS. 1 and 2 illustrate embodiments of restoring a dentin or enamel layer on a tooth, respectively. In FIG. 1, the borate bioactive glass paste 20 is applied to a dentin surface 12 on a tooth, and covered with a cover 18 (e.g. SE bond, Kuraray). The tooth is kept in saliva or an aqueous electrolyte solution such as artificial saliva, and given an effective time of contact between the paste and the dentin, the borate bioactive glass particles degrade into insoluble calcium phosphates 24 and soluble compounds 22. The insoluble calcium phosphates 24 are chemically bound as a layer on the dentin surface 12, and form the restored dentin layer. Then, a water spray 26 may be used to remove the cover 18, the unreacted borate bioactive glass paste 20, and the soluble compounds 22, leaving the tooth 10 with a restored dentin layer.

In FIG. 2, the enamel surface 14 of a tooth is coated with a varnish 28, while leaving an exposed enamel window 30. The borate bioactive glass paste is applied to the enamel window 30 and covered with a cover 18 (e.g. SE bond, Kuraray). Similar to FIG. 1, the tooth is kept in saliva or an aqueous electrolyte solution such as artificial saliva, and over an effective time of contact between the paste and the enamel, the borate bioactive glass particles degrade into insoluble calcium phosphates 24 and soluble compounds 22. The insoluble calcium phosphates 24 are chemically bound as a layer on the enamel surface 14, and form the restored enamel layer. Then, a water spray 26 may be used to remove the cover 18, the unreacted borate bioactive glass paste 20, and the soluble compounds 22, leaving the tooth 10 with a restored enamel layer.

In one embodiment, the method further comprises contacting the cover, a second surface of the tooth, or both, with saliva or an aqueous electrolyte solution after the covering and before the removing. The aqueous electrolyte solution comprises at least one ion selected from the group consisting of 2-130 mmol/L sodium, preferably 5-120 mmol/L, more preferably 10-100 mmol/L;

8-60 mmol/L potassium, preferably 9-40 mmol/L, more preferably 10-36 mmol/L;

1-5 mmol/L calcium, preferably 1.5-4 mmol/L, more preferably 2-3 mmol/L;

0.05-2 mmol/L magnesium, preferably 0.08-1.5 mmol/L, more preferably 0.1-1.0 mmol/L;

5-80 mmol/L chloride, preferably 8-65 mmol/L, more preferably 10-50 mmol/L;

20-90 mmol/L bicarbonate, preferably 25-80 mmol/L, more preferably 30-70 mmol/L; and 1-40 mmol/L phosphate, preferably 2-35 mmol/L, more preferably 3-30 mmol/L.

Preferably the aqueous electrolyte solution comprises all of the previously listed ions. Where the tooth is in the mouth of a patient, the cover and second surface of the tooth may be in contact with saliva or diluted saliva from 20 s-30 min, preferably 30 s-10 min after covering the borate bioactive glass paste with the cover to about 5 s-30 min, preferably 10 s-10 min before removing the cover.

The aqueous electrolyte solution may be considered as an artificial saliva and may be available for in vitro research. The aqueous electrolyte solution may have a pH of 6-8, preferably 6.2-7.4. In other embodiments, an artificial saliva may be an over-the-counter medication, such as Caphosol or NeutraSal. In other embodiments, an isotonic solution may be used. Here, the isotonic solution may be buffered, such as phosphate buffered saline, lactated Ringer's solution, acetated Ringer's solution, or a D5NS intravenous sugar solution, and may have a pH of 7.2-7.5, or about 7.4. In alternative embodiments, cell media, plasma, a fluoride solution, milk, or simulated body fluid may be used.

In one embodiment, one or more components of the saliva, aqueous electrolyte solution, or other solution surrounding the tooth may strengthen or provide stability to the cover. In another embodiment, where the cover is semipermeable, one or more components may diffuse through the cover and strengthen or incorporate with the restored dentin or restored enamel layer.

In one embodiment, the surface of the tooth is within a mouth of a mammal. The mammal may be *Homo sapiens sapiens, Pan troglodytes, Bos primigentus, Sus scrofa domesticus, Canis lupus familiaris, Felis catus, Rattus norvegicus, Mus musculus*, or *Equus ferus caballus*. Preferably, the mammal may be Homo sapiens sapiens. In an alternative embodiment, the borate bioactive glass paste may be applied to materials such as ceramics, ivory, concrete, granite, stucco, or grout.

Dentin hypersensitivity may be caused by exposed dentinal tubules due to a loss of enamel and/or dentin. The method of restoring a dentin layer or enamel layer on a tooth may be used as a treatment for dentin hypersensitivity, as a result of penetrating or occluding the dentinal tubules. As used herein, the terms "treat," "treatment," and "treating," in the context of dentin hypersensitivity refer to the reduction or inhibition in the loss of dentin or enamel, the reduction or amelioration of pain or other symptoms resulting from dentin hypersensitivity, or preventing dentin hypersensitivity from occurring from loss of dentin and/or enamel, or from tooth decay. In one embodiment, borate bioactive glass paste may be applied to an eroded surface of a tooth of a patient who is not experiencing dentin hypersensitivity, in order to prevent the onset of dentin hypersensitivity.

In one embodiment, the borate bioactive glass particles in a solution may degrade to form mineral deposits at a faster rate than other bioactive glasses, such as Bioglass 45S5 or 13-93 bioactive glass. For example, in 20-30 h, a certain initial mass of borate bioactive glass particles may partially degrade to form a calcium phosphate layer having a thickness of 30-50 μm. In that same time, an equivalent initial mass of 45S5 or 13-93 Bioglass under similar conditions may partially degrade to form a mineral layer having a thickness of 10-20 μm. Furthermore, the composition of the borate bioactive glass particles, or the borate bioactive glass paste, may be modified in order to increase or decrease the rate of mineral deposition. For example, borate bioactive glass particles may have different wt % $B_2O_3$ relative to a total weight, or the particles may be formed having different surface area per volume ratios. In one embodiment, borate bioactive glass pastes having different compositions may be used with different types of tooth surfaces, for example, one composition may be used on enamel while another composition is used on dentin. Alternatively, one composition may be used on a surface of a chipped tooth while another composition is used within caries.

According to a fourth aspect, the present disclosure relates to a biocompatible bone graft comprising the borate bioactive glass of the first aspect, a population of osteocompetent stem cells obtained from a mammalian donor, and a growth medium.

Osteocompetent stem cells are stem cells that can differentiate into osteoblast and osteoclast cells. These osteocompetent stem cells may be derived from mammalian stem cell sources such as embryonic or fetal tissue, placental tissue, umbilical cord tissue or blood, menstrual blood, muscle, synovial membrane tissue, bone marrow, periosteum, dermal tissue, or adipose tissue. Preferably, the osteocompetent stem cells are derived from a sample of bone marrow, periosteum, dermal fibroblasts, or adipose tissue. The osteocompetent stem cells for use in the bone graft may be obtained from a primary source or from a cell bank.

The osteocompetent stem cells may be mixed with the borate bioactive glass in the presence of a liquid growth medium to make the biocompatible bone graft. The growth medium may be based on common formulations such as DMEM or DMEM:F12, or the growth medium may be a completely specialized formulation. The growth medium may include common supplements not specific to osteocompetent stem cells, such as fetal bovine serum (FBS), ROCK inhibitor Y-27632, 1-glutamine, sodium pyruvate, or antibiotics. To support the differentiation of the osteocompetent stem cells, the growth medium may include additional supplements and growth factors including, but not limited to, platelet derived growth factor (PDGF), osteopontin, calcium, insulin-like growth factor (IGF-1), β-glycerophosphate, dexamethasone, ascorbic acid-2-phosphate, ascorbic acid, transforming growth factor β (TGF-$β_1$), fibroblast growth factor (FGF), active vitamin D, a bone morphogenic protein (BMP), parathyroid hormone, or any combination thereof. These growth factors may be added individually in a purified form to the growth medium, or they may be added together with their biological source, such as platelet-rich plasma or bone marrow aspirate. In an envisioned embodiment, a growth factor or supplement may be adsorbed onto or chemically attached to the surface of the borate bioactive glass particles.

The biocompatible bone graft may be placed within a bone wound site in a patient. This bone wound site may be a defect resulting from injury such as a transverse fracture, a linear fracture, an oblique fracture, a spiral fracture, a greenstick fracture, or a comminuted fracture; from surgery; from an infection such as osteomyelitis; from malignancy, such as osteoma, osteoid osteoma, osteochondroma, osteoblastoma, osteoblastoma, enchondroma, aneurysmal bone cyst, giant cell tumor of the bone, chondrosarcoma, fibrus dysplasia, osteosarcoma, fibrosarcoma, or Ewing sarcoma; or from a developmental malformation such as a metaphyseal defect. The bone wound site may be in cancellous or cortical bone, or in a single bone wound site that comprises both. The bone wound site may also result from a previous bone graft that became infected or otherwise failed to heal. Preferably the osteocompetent stem cells of the biocompatible bone graft develop osseous tissue in the bone wound site, which is mineralized by calcium phosphate and other minerals from the borate bioactive glass particles.

In another embodiment, the bone graft is implanted with a prosthesis, such as a tooth, a knee, a shoulder, or a hip. The bone graft may also be implanted with an orthopedic implant to support an existing bone or joint, or to replace, in whole or in part, a missing bone or joint. Such orthopedic implants may comprise pins, rods, screws, nails, wires, and plates, and may be made of biocompatible metals such as titanium and related alloys, cobalt-based alloys, or stainless steel, or biocompatible polymeric materials such as carbon fiber, high density polyethylene, ultra-high molecular weight polyethylene (UHMWPE), polymethylmethacrylate (PMMA), or thermoplastic polyether ether ketone (PEEK).

A biocompatible bone graft may be made using the borate bioactive glass in the form of particles, as previously mentioned, or in a different form. For example, the borate bioactive glass may be in a form of nanofibrous scaffolds created by electrospinning. Alternatively, the borate bioactive glass may be in the form of a hierarchical scaffold structure, having interconnected macropores of 80-150 µm, nanopores of 10-100 nm, and surface areas of 100-200 m$^2$/g. A porous borate bioactive glass scaffold may be formed by sintering the borate bioactive glass particles into a certain 3-D shape. In one embodiment, the composition and/or shape of the borate bioactive glass may be modified so that the degradation rate of the glass into soluble compounds and insoluble calcium phosphates approximately matches the bone regeneration rate. For instance, a higher concentration of borate may be used in bone grafts where bone regeneration is faster, such as in a pediatric patient.

The examples below are intended to further illustrate protocols for preparing the borate bioactive glass paste, and using it to restore a dentin layer or an enamel layer on a surface of a tooth, and are not intended to limit the scope of the claims.

EXAMPLE 1

Method of Manufacturing the Borate Bioactive Glass

Borate-based bioactive glass with the composition of 24.4 mol % $Na_2O$, 26.9 mol % CaO, 2.6 mol % $P_2O_5$, and 46.1 mol % $B_2O_3$ was prepared by a conventional melt-quenching method, which is described as follows. Reagent grade $Na_2CO_3$, $CaCO_3$, $H_3BO_4$, and $NaH_2PO_4 \cdot 2H_2O$ were mixed to produce a glass yield of 30 g by using an aluminum mortar. The resulting mixture was put in a Pt crucible and then heated in an electric furnace in air for 1 h at 1450° C. The melt was quenched by pouring it onto a stainless steel plate and was then pressed with another plate to obtain glass plate pieces with the thickness of 0.2-1 mm.

Glass particles (i.e. borate bioactive glass particles) were obtained by crushing the glass using a porcelain mortar and pestle.

EXAMPLE 2

Sample Preparation

Detain Samples

Freshly extracted non-carious third molars were used. The teeth were sectioned to obtain their buccal surfaces, which were then ground flat to expose dentin surfaces at the cervical region. All the dentin surfaces were ultrasonicated in deionized water for 30 s, then etched in 0.5 M EDTA (pH 7.4) for 2 min and rinsed with water spray for 30 s. See Paes Leme AF, et al., *J Dent Res*, 83, 71 (2004)—incorporated herein by reference in its entirety.

Enamel Samples

Third molars were used. The teeth were sectioned to remove their buccal surfaces using a water-cooled diamond saw microtome (1600 Microtome, Leitzwetzlar, Germany) and then ground flat with water-cooled silicon carbide discs (600-and 1200-grade papers; Buehler), and wet-polished using diamond paste to obtain flat enamel surfaces. Two layers of protective nail varnish were applied to protect half of the exposed enamel area, while leaving a treatment enamel window having an area of 2 mm$^2$. All the enamel surfaces were challenged for 4 days with a buffered demineralization solution composed of 2.2 mM $CaCl_2$, 2.2 mM $NaH_2PO_4$, and 50 mM acetic acid, at a pH of 4.5. See Bakry A S, et al., *Dent Mater.*, 30, 314 (2014)—incorporated herein by reference in its entirety.

EXAMPLE 3

Borate Bioactive Glass Paste Application 50 wt % phosphoric acid was prepared by the dilution of 85 wt % phosphoric acid (Wako Chemicals, Osaka, Japan) in distilled water. One-tenth of a gram of the borate glass particles was mixed with 0.2 mL 50 wt % phosphoric acid to form a gel with a pH of 2. The acidic paste (i.e. borate bioactive glass paste) was immediately applied to the dentin surfaces of group III and IV specimens by microbrush (Microbrush International, Grafton, Wis., USA). A layer of bonding agent (Clearfil SE Bond, Kuraray-Medical, Tokyo, Japan) was immediately applied over the borate glass-phosphoric-acid gel and then light-cured.

After storage in artificial saliva for 24 h, the thin layer of the bonding agent was gently removed by means of an excavator, and then rinsed with water spray for 30 s.

EXAMPLE 4

FE-SEM/EDS Interface Examination

Figure 3:
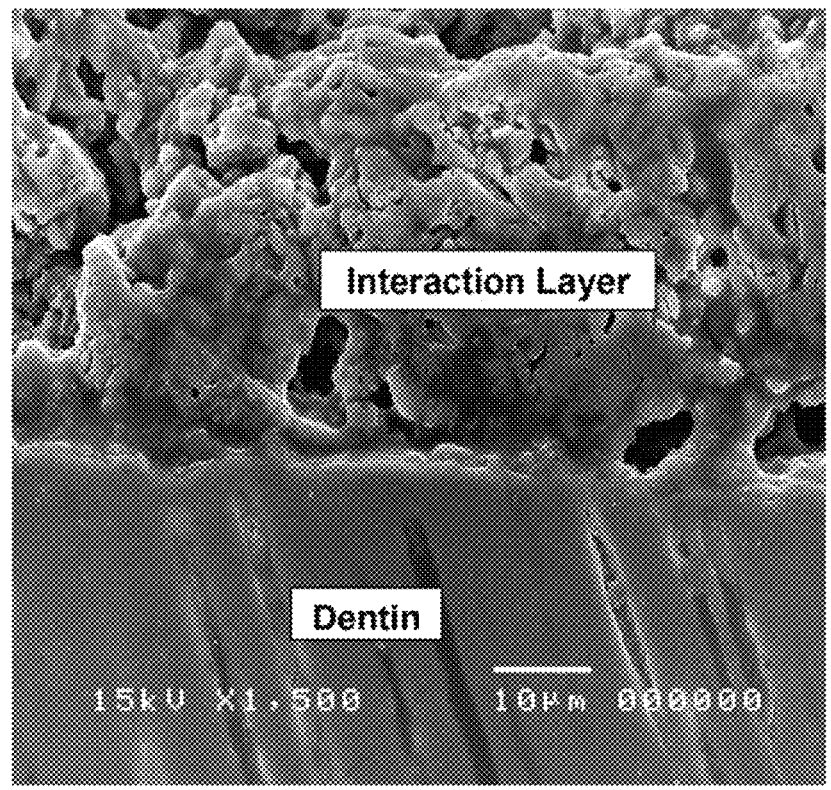
FIG. 3 is an FE-SEM image of a tooth cross-section having an interaction layer of calcium phosphate deposited on the dentin surface.

The specimens were stored in de-ionized water for 24 h, and then sectioned perpendicularly to the interface to produce 1.5 mm-thick slabs. The cut surfaces were polished, etched, gold-coated, and then examined by FE-SEM/EDS (S-4500, Hitachi, Hitachinaka, Japan). See Bakry A S, et al., *J Adhes Dent.*, 9, 513 (2007)—incorporated herein by reference in its entirety. Line scans were done across the treated dentinal surfaces with an EDS attachment for the following elements: phosphate, calcium, and silicon. FIGS. 3 and 4A show these FE-SEM images of the deposited calcium phosphate "interaction layer" on the dentin surface of a specimen. FIG. 4B furthermore shows an EDS line scan of phosphate, calcium, and silica corresponding with the dotted line in the FE-SEM image of FIG. 4A. The EDS line scan shows that the interaction layer and the dentin contain similar amounts of calcium phosphate, while both contain negligible amounts of silica.

The invention claimed is:

1. A borate bioactive glass paste, comprising:
   20-60 wt % of a borate bioactive glass in the form of particles,
   the borate bioactive glass comprising:
   40-60 wt % $B_2O_3$;
   15-25 wt % CaO;
   15-25 wt % $Na_2O$; and
   2-15 wt % $P_2O_5$;
   each relative to a total weight of the borate bioactive glass,
   and
   40-80 wt % phosphoric acid solution,
   each relative to a total weight of the borate bioactive glass paste.

2. The borate bioactive glass paste of claim 1, wherein the borate bioactive glass is substantially free of $SiO_2$ or MgO.

3. The borate bioactive glass paste of claim 1, wherein the borate bioactive glass further comprises at least one compound selected from the group consisting of $Ca(PO_3)_2$, $K_2O$, $Al_2O_3$, $TiO_2$, $CaF_2$, $Fe_2O_3$, CuO, SrO, $Bi_2O_3$, $Ce_2O_3$, $Ga_2O_3$, and ZnO, and
   wherein each of the at least one compound is present in the borate bioactive glass at a weight percentage of 0.5-25 wt % relative to a total weight of the borate bioactive glass.

4. The borate bioactive glass paste of claim 1, wherein the borate bioactive glass is in the form of particles having longest dimensions of 1-200 μm.

5. The borate bioactive glass paste of 1, further comprising a salt selected from the group consisting of $KNO_3$, NaF, $SnF_2$, $SrCl_2$, and $CaCl_2$,
   wherein the salt is present at a weight percentage of 0.1-10 wt % relative to a total weight of the borate bioactive glass paste.

6. The borate bioactive glass paste of claim 1, further comprising silica particles having diameters of 1-100 μm,
   wherein the silica particles are present at a weight percentage of 1-50 wt % relative to a total weight of the borate bioactive glass paste.

7. The borate bioactive glass paste of claim 1, which has a bulk viscosity of 5,000-100,000 cP at 25-38° C.

8. The borate bioactive glass paste of claim 1, which has a pH of 1-3, and wherein the phosphoric acid solution is an aqueous solution of 25-85 wt % phosphoric acid relative to a total weight of the phosphoric acid solution.

9. The borate bioactive glass paste of claim 1, further comprising a gelling agent,
   wherein the gelling agent is present at a weight percentage of 0.1-20 wt % relative to a total weight of the borate bioactive glass paste.

10. A method of restoring a dentin layer or an enamel layer on a surface of a tooth comprising:
    applying the borate bioactive glass paste of claim 5 onto the surface of the tooth,
    covering the borate bioactive glass paste with a cover,
    maintaining contact between the borate bioactive glass paste and the surface of the tooth for an effective time for forming a restored dentin layer or a restored enamel layer between the borate bioactive glass paste and the surface of the tooth, and
    removing the cover and the borate bioactive glass paste.

11. The method of claim 10, wherein the cover is at least one selected from the group consisting of a resin, a varnish, a sealant, a bonding agent, a cement, a wax, a dental composite, a cap, a plug, a band, and a dental appliance.

12. The method of claim 10, wherein the cover is semi-permeable.

13. The method of claim 10, wherein the surface of the tooth has exposed dentinal tubules.

14. The method of claim 10, wherein the surface of the tooth is within a dental cavity.

15. The method of claim 10, wherein the effective time is 6 hours-14 days.

16. The method of claim 10, further comprising contacting the cover, a second surface of the tooth, or both, with saliva or an aqueous electrolyte solution after the covering and before the removing,
    wherein the aqueous electrolyte solution comprises at least one ion selected from the group consisting of
    2-130 mmol/L sodium,
    8-60 mmol/L potassium,
    1-5 mmol/L calcium,
    0.05-2 mmol/L magnesium,
    5-80 mmol/L chloride,
    20-90 mmol/L bicarbonate, and
    1-40 mmol/L phosphate.

17. The method of claim 10, wherein the surface of the tooth is within a mouth of a mammal.

* * * * *